(12) United States Patent
Belotserkovsky et al.

(10) Patent No.: US 6,191,430 B1
(45) Date of Patent: Feb. 20, 2001

(54) GEL POINT SENSOR

(75) Inventors: Edward Belotserkovsky, San Francisco; John A. Dahlquist, Palo Alto, both of CA (US)

(73) Assignee: Honeywell International, Morristown, NJ (US)

( * ) Notice: Under 35 U.S.C. 154(b), the term of this patent shall be extended for 0 days.

(21) Appl. No.: 09/196,891

(22) Filed: Nov. 20, 1998

(51) Int. Cl.⁷ .................................................. G01N 21/86
(52) U.S. Cl. ...................... 250/559.16; 356/446; 356/429
(58) Field of Search ...................... 250/559.01, 559.16, 250/559.29, 559.32; 356/429, 446, 448

(56) References Cited

U.S. PATENT DOCUMENTS 4,945,253 * 7/1990 Frohardt ........................... 250/559.16
5,640,244 * 6/1997 Hellstrom et al. .

* cited by examiner

Primary Examiner—Seungsook Ham
Assistant Examiner—Kevin Pyo
(74) Attorney, Agent, or Firm—Anthony E. Ebert

(57) ABSTRACT

A comparison of the specular and diffused radiation reflected from a coating can be used in ratio to locate the gel point of the coating, and to monitor coating drying characteristics. This same system may be used to monitor the drying process of the coatings in a lab setting to characterize the drying process, optimize coating quality or optimize mill efficiency. A system implementing the Applicant's method uses a radiation source to illuminate a measurement location on the coating, and then provides a first and second radiation detectors to detect reflected radiation from the coating, originating from the radiation source. One of the radiation detectors is arranged to collect specular radiation. The second detector is arranged to collect only diffused radiation. The ratio of these two values represents information about the location of the gel point for the coating, and coating drying characteristics.

19 Claims, 6 Drawing Sheets

GEL POINT SENSOR

BACKGROUND OF THE INVENTION

1. Field of the Invention

The present invention relates generally to monitoring of coatings applied to webs or sheets. More particularly, this invention relates to a method of monitoring the drying speed of these coatings.

2. Description of the Prior Art

Application of coatings to sheets or webs of material is a common process in a number of different industries. Particularly in the paper industry, coatings, containing components such as clay, latex, or $CaCO_3$, are used to affect the absorption, stability, gloss, printability or other characteristics of the underlying web or sheet. In other industries, such as plastic, the coating may be the most important part of the product (i.e. photographic coating).

In an on-line setting, coatings are typically applied using numerous types of coating devices (i.e. coaters). Typically, these devices hold the coating in liquid form, suspended in a solvent, such as water, to ease application and improve bonding to the base sheet. A blade or knife is used to spread the coating along the base sheet as it moves past the coating device. The coating device is followed by one or more drying devices (i.e. dryers) which evaporate the solvent out of the coating, using heat and/or moving air, leaving a sold or semisolid coating layer behind on the base sheet.

The speed at which the coating dries can be a critical factor in coating quality and the quality of the final sheet product, as well as a factor in mill or plant efficiency, and the amount energy used during the coating application process. Factors which effect coating drying speed include the mill environment, coater settings, dryer settings, base sheet properties, as well as the quantity and type of components in the coating. Further, the type and amount of solvent—which evaporates and/or is absorbed by the base sheet upon drying of the coating—also effects the drying time of the coating.

As the reader is likely aware, the quality of applied coatings is important for a number of reasons. Visible variations in quality and uniformity of a coated sheet are clearly something which should be avoided. Further, non-visible variations can be critical where an applied coating is to be used as the base for further processing, such as printing. Lastly, a coating may provide mechanical durability and protection against environmental factors such as moisture, heat or sunlight.

The speed at which a coating dries effects coating quality and final sheet quality in a number of ways. When the sheet is wet, the heat in the dryers is absorbed by the coating as the coating solvent proceeds through a state change from a liquid to a vapor. Once the coating or coating surface is dry (i.e. most of the coating solvent has evaporated) however, the excess heat is no longer absorbed by the coating solvent. Rather, it is absorbed by the base material and coating, which may burn or crack easily in their dry state. If, on the other hand, the coating dries too slowly, the coating may be smeared or stick to manufacturing line components, or other sections of the sheet (i.e. if the sheet is rolled while the coating is still wet). Thus, monitoring drying speed can be used to improve overall coating and final product quality, as well as prevent product waste.

Monitoring coating drying speed has another advantage as well. It can reduce the amount of wasted energy and increase dryer lifetime by allowing unneeded drying devices to be turned off or selected drying devices to be set at lower temperature settings, when the coating dries prior to the end of a section of coating dryers. Turning off unneeded dryers in fact, is one method of preventing the sheet from being burned or otherwise damaged due to the excessive heat in the dryers.

Currently, temperature sensors are used to monitor when a coating is dry in many sheet mills and plants. Typically, the temperature sensors are located in or near the dryers following the coater, and register an increase in sheet temperature when the coating is dry. Due to the harsh temperature in these drying environments, thermocouples or other rugged temperature devices are preferred to measure temperature within the dryers. Unfortunately, thermocouples are a relatively slow temperature-measuring device compared with the speed at which the sheet is moving past the dryers. Using temperature to monitor the drying speed of the coatings is also disadvantageous because once the temperature sensors register the increase in sheet temperature, damage to the sheet may have already occurred due to over-drying.

While remotely-located IR temperature sensors have also been used, these types of sensors are not very accurate, and their readings depend on surface emmisivity, which changes during drying.

Ideally, monitoring of drying speed would be accomplished by monitoring the location of one or more "gel points" of the coating. The gel point defines the time at which particular coating components form semisolid networks of solid aggregates, as the coating solvent evaporates from the applied coating layer. When most or all the primary coating components have reached this gel point, the coating is effectively considered to be dry.

Currently, no device exists to monitor the gel point of coatings on sheets or webs of material.

SUMMARY OF THE INVENTION

The present invention addresses the need for a means and apparatus to monitor the drying speed of coatings on a web or sheet of material, utilizing a coating's gel point. In the Applicant's system, a sensor is used to compare specular and diffused radiation reflected from the coating. In a particularly preferred embodiment, the specular and diffused radiation are used in ratio to locate the gel point.

In an on-line system, with the gel point known, coating drying speed can be increased or decreased, coating composition may be altered, or coating or drying device settings may be changed to suit the designer's needs. The designer's choice of actions may be based on such factors such as coating or final product quality or uniformity, or mill efficiency.

In an off-line system, the gel point may be used to compare the drying time of different coating formulations or base materials, develop drying or coating device configurations, or troubleshoot coating problems.

A system implementing the Applicant's method may be achieved by directing a beam of radiation from a radiation source at a measurement location on the coating, and providing a first and second radiation detectors which examine the coating at the measurement location. One of the radiation detectors is situated to collect specular radiation, while the other radiation detector is situated to collect only diffused radiation. The ratio of these two values is used to determine the location of the gel point relative to the measurement location, or in an off-line system, to produce characterization curves of the ratio of these two values for a monitored drying coating.

One object of the invention is to provide a non-contacting method for monitoring the drying speed, gel point and drying characteristics of a coating.

A further object of the invention is to provide a simple, compact, coating condition-measuring sensor with improved accuracy and speed.

An even further object of the invention is to provide a multi-sheet characteristic measurement system which includes measurement of coating gel point.

A further object of the present invention is to provide a system for the lab investigation (i.e. off-line) of different types of coatings, their drying speeds, and drying characteristics.

Further advantages of the Applicant's system will become apparent upon reading of the detailed description to follow.

DETAILED DESCRIPTION

Figure 1:
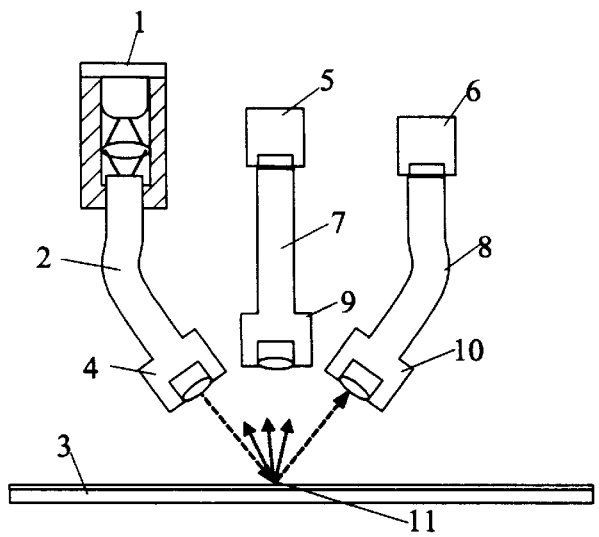
FIG. 1 shows an embodiment of the Applicant's inventive gel point sensor utilizing fiber optic cables.

FIG. 1 shows one embodiment of the Applicant's inventive gel point sensor. In the figure, radiation from radiation source 1,—in this case a laser diode—is transported via fiber optic cable 2 to a location close to the surface of the coating 3, to be examined. The light source may be any number or type of broad-band or narrow band source. For example, regular light bulbs and LED's would both be suitable alternate radiation sources to the one shown. A means for directing the beam of radiation—such as a lens—otherwise identified as an optical manipulation device 4, focuses or collimates the radiation into a beam and projects the beam onto the coating, 3, at measurement location 11.

The coating overlies a substrate material such as paper, plastic, glass, metal, fabric or other material. The type of coating under examination may be any type of coating exhibiting a change in optical reflectance properties from its wet state to its dry state. For example, the surface to be measured may be paper or Mylar coated with compositions of latex, clay, calcium carbonate, silicone or plastic. Other types of coatings on either paper or other types of substrate material will be known to one of skill in the art as suitable for the Applicant's invention, based on the description to follow.

A first and second radiation detectors 5 and 6, examine diffused radiation and specular radiation, respectively, reflected from coating 3, at measurement location 11, via fiber optic cables 7 and 8, respectively. Optical manipulation devices 9 and 10—such as lenses or optical filters—collect radiation reflected from the coating before it passes into fiber optic cables 7 and 8.

Optical manipulation device 9 is placed so that it will only receive diffused radiation from coating 3 (i.e. not specular radiation), while optical manipulation device 10 is placed so that it will receive primarily specular radiation from coating 3. The simplest method of arranging the optical manipulation devices to is to angle the radiation source at a first angle relative to the normal to the surface of the coating, and angle optical manipulation device 10 at the negative of this angle, relative to the normal to the surface of the coating. Optical manipulation device 9 may be placed anywhere outside this angle to receive only diffused radiation.

For example, one set of workable angles would be to place optical manipulation device 9 perpendicular to the paper surface, and place optical manipulation device 10 and optical manipulation device 4 at angles of approximately 30° and −30°, relative to the normal to the surface of the coating. Angles as low as approximately 5° may work, however, as well as much higher angles.

Optical manipulation devices 4, 9 and 10 typically contain a lens for focussing radiation into or out of the fiber optic cables. These devices may contain more complicated components, such as filters, splitters, etc., as is required for the reader's design or application. While the gel point sensor of FIG. 1 has been shown and described using optical manipulation devices 4, 9 and 10, these components could be eliminated under certain conditions. Any system without them however, must still focus or collimate radiation projected against the surface of the coating. Further, any such system must cause only diffused radiation to reach radiation detector 5, and primarily specular radiation to reach radiation detector 6.

Radiation detectors 5 and 6 may comprise bolometers, IR cells, photocells, or other types of detectors which can monitor infrared radiation. Filters may be incorporated into the radiation detectors to isolate particular frequencies of radiation to be measured. The radiation detectors may be of the same or different types, or may examine the same or different parts or portions of the spectrum of radiation received from radiation source 1.

Use of fiber optic cables to implement the Applicant's invention is preferred where excessive heat near the sheet could easily damage the sensor components. However, other means may be used to channel the diffused and specular radiation reflected from the coating. For example, in the drying devices following the coater in a paper machine, the temperature near the paper may be in the hundreds of degrees. Therefore, fiber optic cables would be used to locate the radiation detectors remote from the sheet in a cooler location. Where heat is not an issue the fiber optic cables may be eliminated in lieu of radiation detectors local to the measurement location. For example, in some instances a gel point sensor may be placed just prior to the coating dryer of a paper machine, where it can serve as a reference for a second gel point sensor within the one or more dryers. This reference gel point sensor would not be subject to the high temperature conditions inside the dryers. Thus, the fiber optic cables could be eliminated, and the radiation detector components could be located local to the coating surface. Of course, the applicant contemplates that future radiation detector designs (more rugged sensors or built-in cooling means) may allow use of sensors which can operate in harsh environments, such as within the drying devices of a paper machine. In these cases, fiber optic cables could be eliminated, even in where harsh conditions do exist.

In any event, in operation of the gel point sensor of FIG. 1, radiation source 1 projects a beam of radiation against the coating via fiber optic cable 2 and optical manipulation device 4. Radiation detectors 5 and 6, via fiber optic cables 7 and 8 and optical manipulation device 9 and 10 respectively, examine radiation reflected from the coating. Radiation detector 5 examines diffused radiation from the coating to produce a diffused radiation value or signal, while radiation detector 6 will examine specular radiation to produce a specular radiation value or signal.

A computing device or means, such as a computer or microcontroller receives and compares the radiation detector signals or values from radiation detectors 5 and 6. The comparison of the specular and diffused radiation values can be facilitated by creating a ratio of the values from the two detectors. From this ratio, information about the gel point or coating drying characteristics can then be extracted.

The ratio between the specular and diffused radiation values from the radiation detectors may be written as:

$$R=S_1/S_2, \text{ where,} \quad (1\text{---}1)$$

$S_1$=diffused radiation value, and
$S_2$=specular radiation value.

The ratio R, may be called, and will be referred to as the gel point sensor output or output value.

Prior to the gel point of the coating being examined, the coating is highly reflective, producing little or no diffused radiation. Therefore, the value produced by radiation detector 5, $S_1$, will be near zero, and the value produced by radiation detector 6, $S_1$, will be notably larger than zero. Thus, a ratio of the diffused radiation value to the specular radiation value before the gel point will be roughly zero.

After the gel point, the specular and diffused radiation values will be closer to each other with a larger portion of the radiation formerly specularly reflecting, now diffusing. A portion of this newly diffused radiation will reach radiation detector 5. Thus, the ratio, R, of diffused to specular radiation becomes a value closer to one.

Functionally, scaling or other processing, sensor output differences, or other factors may effect the apparent ratio in the computer or microcontroller. These factors may be eliminated during calibration, if desired. For example, the voltage output of the specular and diffused sensors may be scaled differently or may be offset in voltage from each other. To adjust for this, the sensor outputs may be normalized using one or more standard calibration tiles as a reference prior to gel point sensor use. Alternately, the sensor output, R, may be scaled to a different range then zero to one, for easier amnipulation.

The exact range of the ratio of diffused radiation to specular radiation will depend on the radiation detector types, the amount of total diffused radiation collected, and the type of coating being measured, among other factors. For example, a dry glossy coating will provide a much lower gel point sensor output value than a dry mat coating. By physical examination of the coating, or other methods, the ratio value for different types of coatings in wet and dry states may be determined. These predetermined values may then be used as standards to identify gel point during on-line measurements. With the gel point known, appropriate control actions may then be taken to effect coating or final product quality or mill efficiency.

Figure 2:
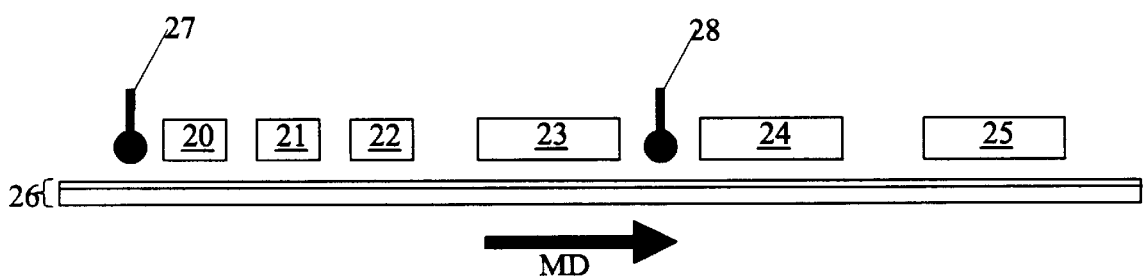
FIG. 2 shows a schematic diagram of an arrangement of drying devices and one possible placement of the Applicant's gel point sensors among the drying devices.

The integration of the Applicant's sensor into a section of coating dryers in a paper machine is now described. FIG. 2 shows a side view of the section of drying devices. Infrared dryers 20, 21 and 22 lie up-machine of three air dryers 23, 24 and 25. Paper 26, moving from left to right across the drawing, is covered by a wet coating, applied just prior to infrared drier 20.

A first gel point sensor 27 is placed just subsequent to coating application, and just before first infrared dryer 20. Gel point sensor 27 provides a known value for the ratio of diffused to specular radiation for the wet coating. A second gel point sensor 28 is placed at some further point along the section of drying devices. In the figure, sensor 28 is located between first and second air dryers 23 and 24. The value produced by gel point sensor 28 provides an intermediate reading for the ratio of diffused to specular radiation.

The reading from gel point sensor 27 can be used as a reference or base-line for the reading from gel point sensor 28. For example, gel point may be defined as a certain percentage increase in the gel point sensor output, R, from the gel point sensor 27 location to the gel point sensor 28 location.

Figure 3:
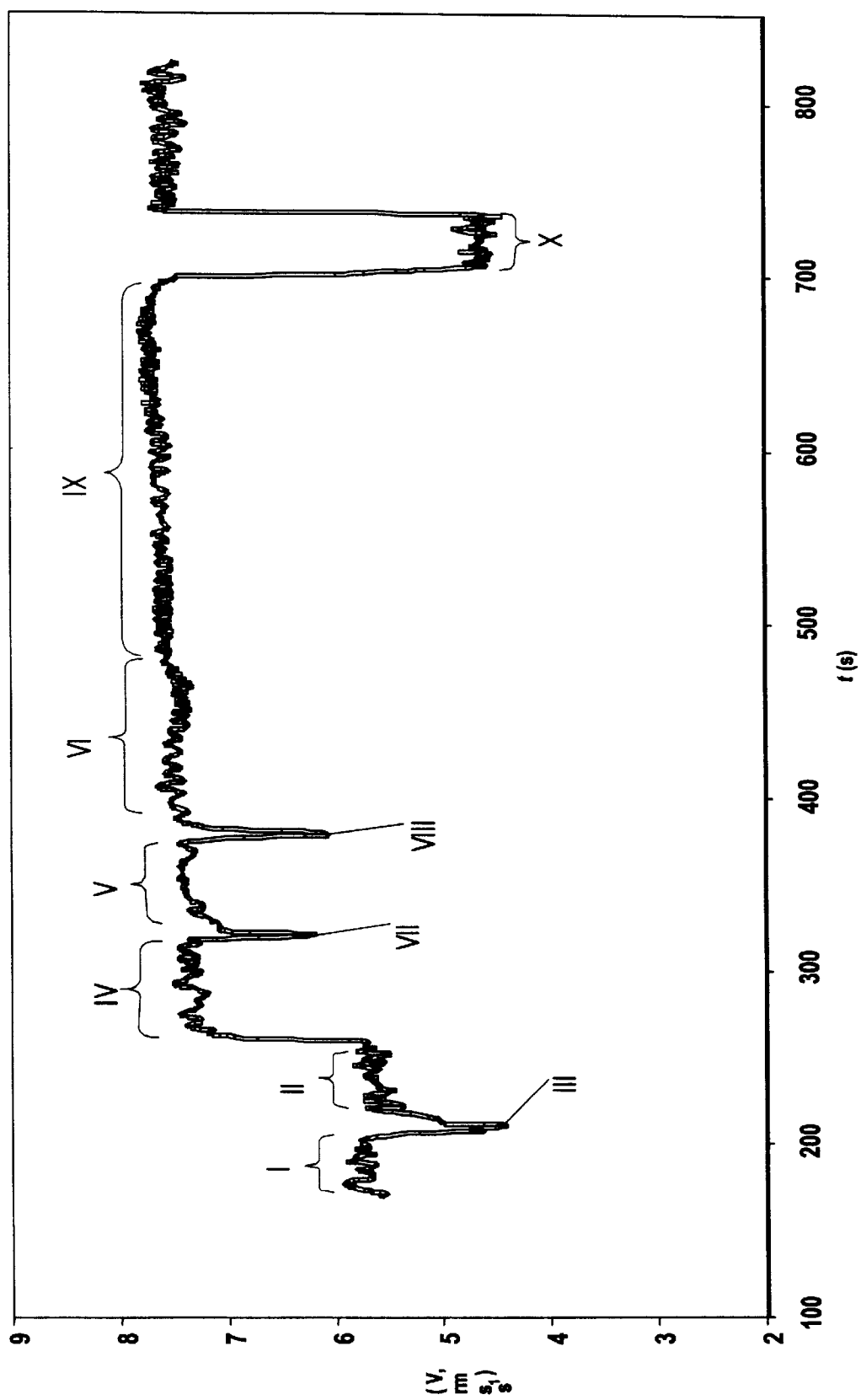
FIG. 3 shows a graph of gel point sensor output from the system of FIG. 2.

The graph of FIG. 3 shows the output, $S_1$, of gel point sensor 28 versus time, t. The spikes and dips in the graph show times when various infrared dryers were turned off and on to examine how each effects the gel point of the coating. Graph sections labeled I and II show the gel point sensor 28 output when a single infrared dryer is operating. The sharp drop labeled III indicates a momentary turning off of the single infrared dryer. Sections labeled IV, V and VI represent times when two infrared dryers are on. Sharp drops labeled VII and VIII represent momentary shutting off of one of the two operating infrared dryers. The Section labeled IX represents times when all three infrared dryers are on. The valley labeled X represents a momentary turning off then on again of all three infrared radiation dryers simultaneously.

To make use of the data of the graph of FIG. 3, the designer must have pre-selected the gel point sensor output or output range, $S_1$, which represents a dry coating. For example, the designer may have determined that a sensor output, $S_1$, at or above 7 volts represents a dry coating in FIG. 3, while gel point sensor output, $S_1$, below 7 volts in FIG. 3 indicates a wet coating or one below the gel point. This may have been determined, for example, by using an independent drying speed measurement means, an off-line gel point sensor, or by visual or tactile inspection.

Assuming 7 volts in FIG. 3 represents when a dry coating is passing through gel point sensor 28 of FIG. 2, it can be seen that only two of the three infrared dryers (and one air dryer) are necessary to dry the coating, since turning on the third infrared dryer does not result in any significant gel point sensor 28 output change, as indicated by the transition from section VI to section IX of the graph. Further, since the output from gel point sensor 28 is above 7 volts after first air dryer 23, second and third dryers 24 and 25, are not required, as the coating is already dry after just first air dryer Of course, with the addition of more gel point sensors to the system shown in FIG. 2, a more accurate placement of the gel point may be determined. For example, by placing a gel point sensor between the third infrared dryer 22 and the first air dryer 23, the user could determine if the gel point occurs before, or within, the first air dryer. This determination would lead to the first air dryer being turned off, or prompt a reduction in IR dryer temperature, for example, if the gel point occurs before the first air dryer.

Alternately, or additionally, a gel point sensor may be placed between second and third air dryers, 24 and 25, and one or more infrared dryers may be turned off or temperature-adjusted, to determine if the second and third air dryers will completely dry the paper, with less infrared dryers on. Further, because of the simplicity of the Applicant's gel point sensor design, placement of multiple gel point sensors in this manner is not cost prohibitive.

As those of skill in the art will be aware, a sheet forming machine may be used for more than one grade or type of web or sheet, and each sheet and/or coating type will typically have a different drying speed. Thus, by adding a gel point sensor after each dryer, on-line continuous control may be use to continually re-assess the need for more or less dryers or new dryer settings, with little manual intervention or experimentation with different dryer configurations. The primary advantage of this close monitoring and control of the drying devices is that it prevents damage or degradation to the coating and underlying sheet. However, plant efficiency and dryer life can also be improved, as no unnecessary energy is spent operating the dryers once the sheet is dry.

While control of the drying devices following the coating section has been used as an example, the gel point, and the gel point sensor output, may be used to perform other actions in the sheet mill or plant. The gel point sensor, for example, may be used to alter coating device settings, line speed, coating composition, or any other number of factors.

Figure 4:
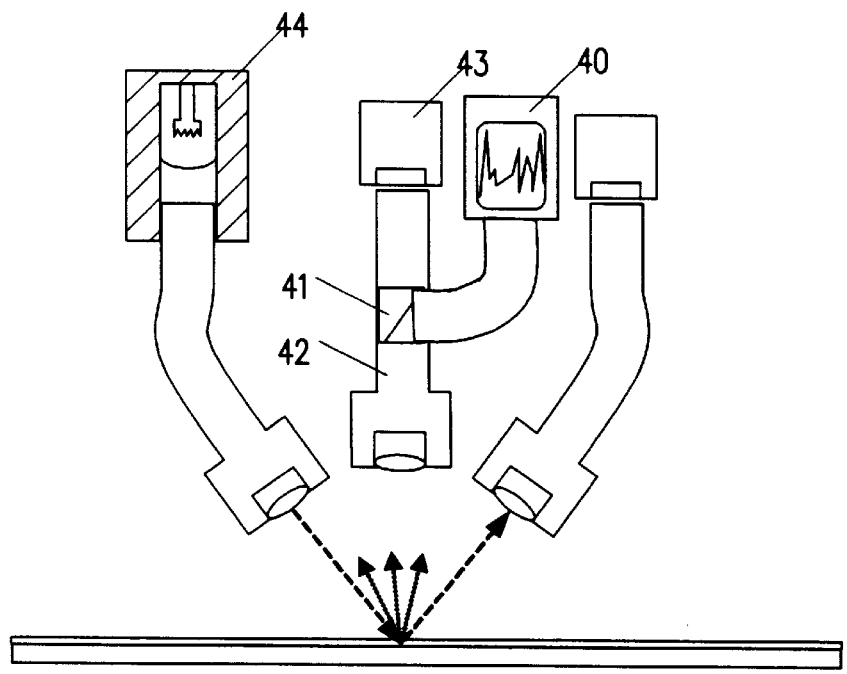
FIG. 4 shows an embodiment of the Applicant's invention which includes a gel point sensor, along with a second sensor means for measuring selected secondary characteristics of the coating or underlying sheet.

The Applicant's basic gel point sensor of FIG. 1 may be combined with further sensor means for taking other types of measurements and/or for monitoring other sheet characteristics. A spectrometer, for example, might be provided for this function. FIG. 4 shows the gel point sensor of FIG. 1 modified with the addition of a spectrometer 40, which receives diffused radiation via optical splitter 41 and from the same fiber optic cable, 42, as used to pass radiation to diffused radiation detector 43. While the radiation source for the gel point sensor of FIG. 1 was not subject to any specific requirements, the radiation source for the gel point sensor of FIG. 4, labeled 44 in the figure, must be a broad-band radiation source to provide the desired range of radiation frequencies to the spectrometer. In the figure, a simple light bulb is used as the broad-band source. The remaining parts of the gel point sensor may be the same as in FIG. 1.

Spectrometer 40 likely will measure at least a second sheet characteristic different from that measured by gel point sensor 3, but more likely will measure a plurality of other sheet characteristics. Further, while a spectrometer has been mentioned, other types of sensors are also possible, in lieu of the spectrometer, such as a second bolometer, other types of infrared detectors, acoustic-based devices, or other components.

Figure 5:
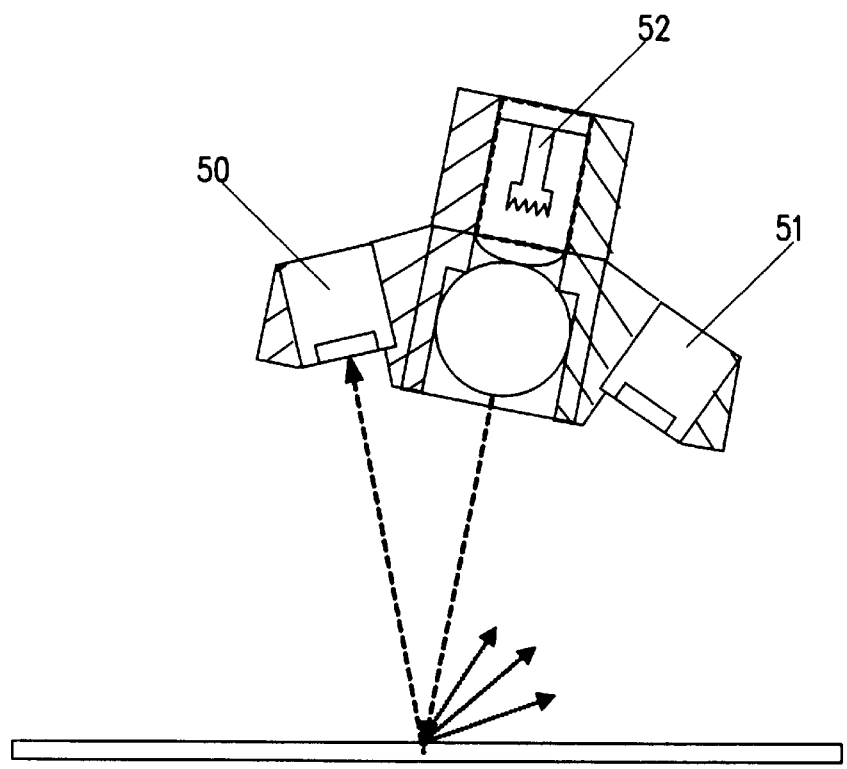
FIG. 5 shows an embodiment of the Applicant's gel point sensor utilizing compact source and detectors, and which localizes the source and detectors near the coating surface.

A gel point sensor which eliminates fiber optic cables from the Applicant's design is shown in FIG. 5. In the figure, two radiation detectors 50 and 51, on either side of a radiation source 52, serve as specular and diffused radiation detectors, respectively. The gel point sensor is tilted to cause detector 50 to receive primarily specular radiation reflections from the coating, and only diffused radiation reflections to reach radiation detector 51. The system of FIG. 5 would be useful, for example, in applications where the gel point sensor would not be subject to extreme heat, such as reference gel point sensor 27 in FIG. 2, for off-line gel point measurements, or if a cooling system is added to the gel point sensor. Cooling could be provided, for example, by a fan, refrigerant, heat shielding, or other means.

The gel point sensor of FIG. 5 may also be used in conjunction with other functions for the system, such as measuring basis weight, gloss or fiber orientation. As one of skill in the art will be aware, many sheet property measurements use diffused radiation, rather than specular radiation.

Thus, to use the system of FIG. 5 to make these other types of measurements the sensor unit may be pivoted between two orientations, or other radiation detectors in the sensor unit, properly angled, may be used to take these other types of measurements.

While the system described so far has valuable use for on-line measurement, the Applicant's system may also be used effectively to monitor, characterize or troubleshoot coatings during drying, in an off-line setting. Monitoring of drying characteristics may be useful to determine the effect of different coating compositions on drying time, to relate these factors to coating quality, to identify the source of coating quality problems, or simply to develop drying schemes for different coatings and base materials. Further, the off-line data may be used to help calibrate the on-line gel point sensor systems.

Figure 6:
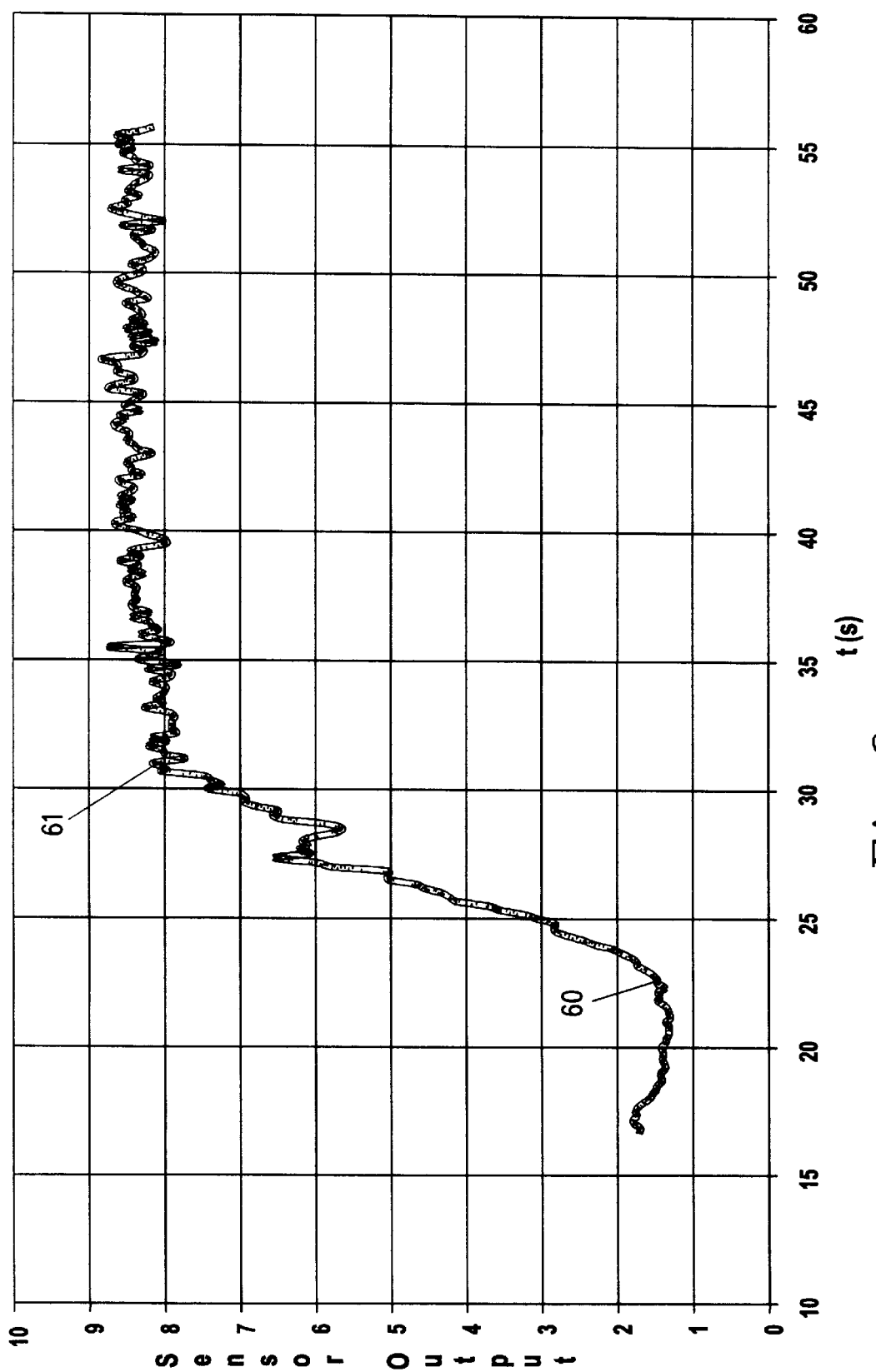
FIG. 6 shows gel point sensor lab data for a gloss coating on Mylar.

FIG. 6 shows a typical drying curve for a laboratory "draw-down" (i.e. manually applied coating) on Mylar. In the Figure, the y-axis shows sensor output, R, scaled by 10, vs. time. Typically, the coating engineer is interested in the first and second critical solid locations in the drying curve. The first critical solids location is where the ratio curve turns upward, labeled 60 in the graph of FIG. 6. The second critical solids location is where the curve turns back to the horizontal, labeled 61 on the graph of FIG. 6.

The first critical solids location for example, determines how soon, after the start of drying, the coating solvent begins to vaporize. If this point occurs too quickly, the surface of the coating may dry before the underlying coating has had a chance to dry. This will not only reduce the drying efficiency of the underlying coating, it may lead to cracking or bubbling due to differential contraction of the coating surface and coating interior. The second critical solids location, which is typically examined with reference to the first critical solids location, is used to examine the slope of the drying curve. The slope will determine the temperature settings for, and the number and types of drying devices necessary, as well as the maximum drying speed at which the sheet may be moved through the line. If the slope is too steep, it may be difficult to track when drying occurs, and thus there is more likelihood that damage to the sheet or coating may occur due to overdrying. If the slope is too shallow, the speed of an on-line process using that coating may have to be slowed down an undesirable amount to allow the coating to dry.

The shape of the drying curve may also be useful, as it can provide clues into intermediate drying points, multiple solvent vaporization locations, or other process characteristics.

With the information provided by the off-line graphs, the coating composition or thickness, line speed, coating device operation, heating device operation or other process factors may be adjusted to achieve the best coating product. The information may also be used to trouble shoot coating problems which cannot be solved with other means.

Figure 7:
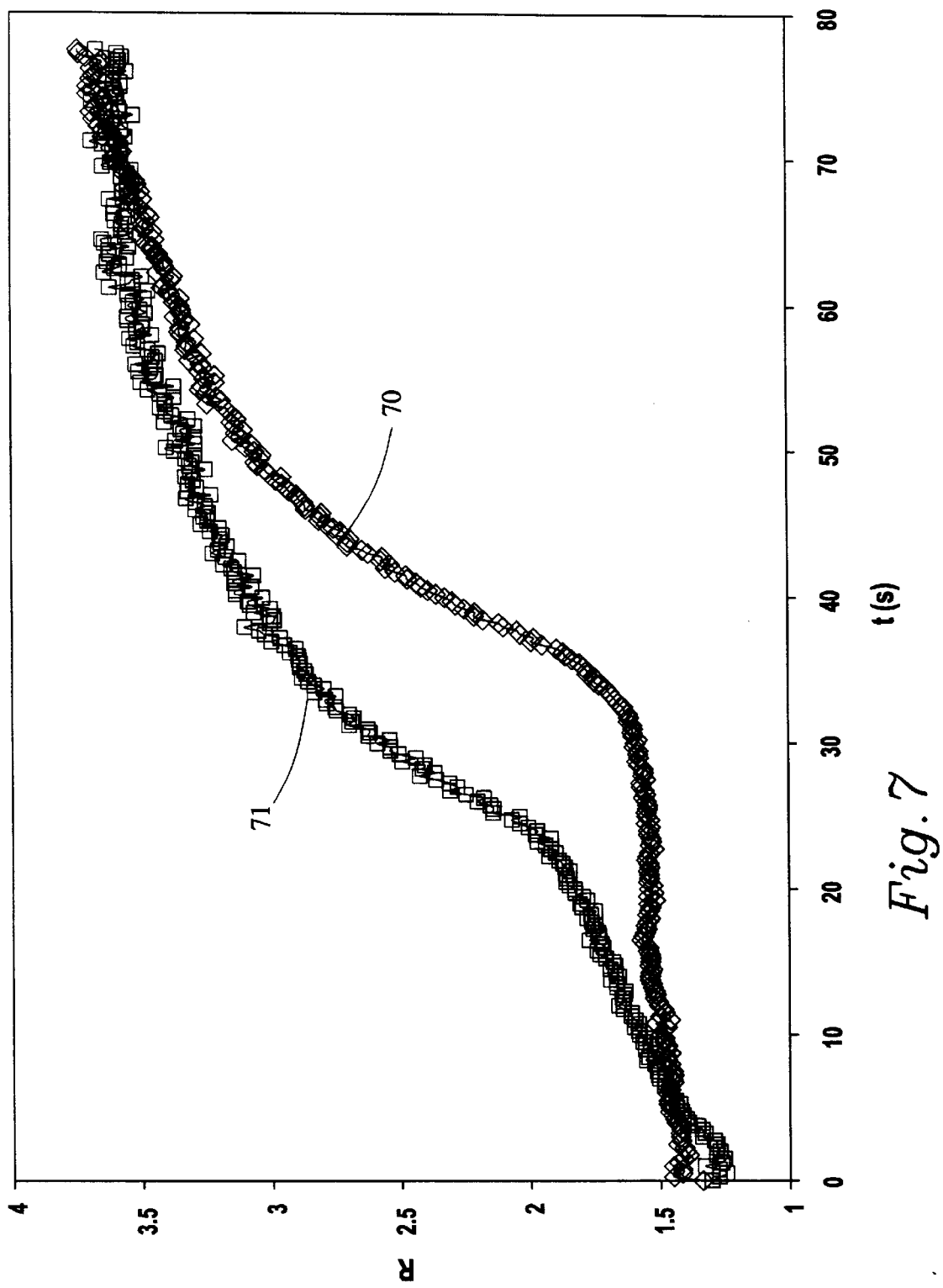
FIG. 7 shows a comparison of gel point sensor data for a gloss coating and a dull coating on the same paper grade.
Figure 8:
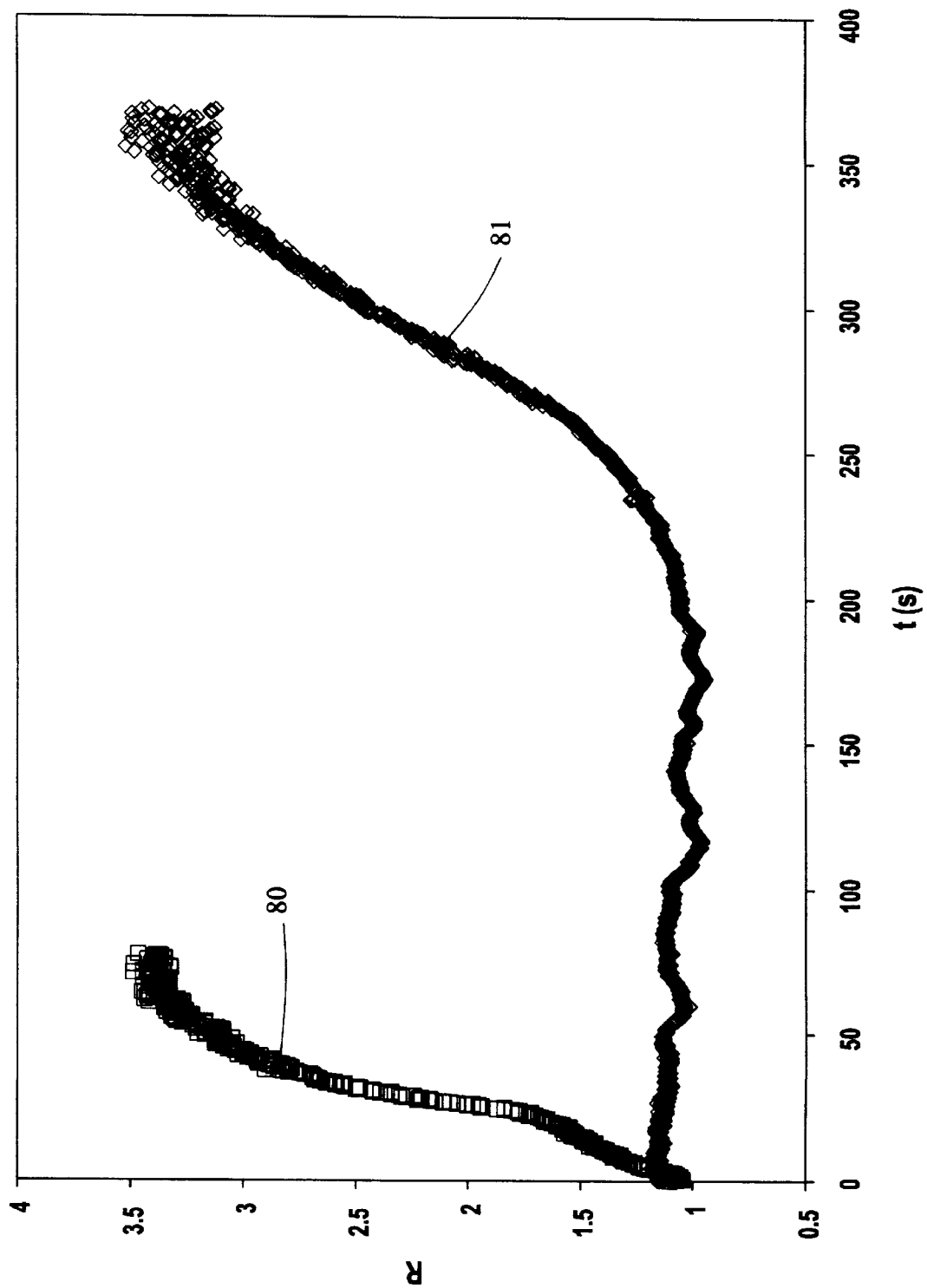
FIG. 8 shows a comparison of gel point sensor data for a gloss coating applied to Mylar and the same gloss coating applied to paper.

The off-line system is also useful in comparing the effects of different base materials or coating composition variations on drying time. For example, FIG. 7 shows a comparison of the gel point sensor output, R, of a dull coating on paper versus the gel point sensor output of a glossy coating on paper. In the figure, the dull coating is labeled 70 and the glossy coating is labeled 71. In the graph of FIG. 8, the gel point sensor output of a gloss coating on Mylar, 80, is plotted versus the gel point sensor output of the same gloss coating on paper. In both FIGS. 7 and 8, clear differences in drying characteristics can be seen.

Such graphs, produced off-line, may be used to program the drying/coating section of the mill, for example, so that types of coatings may be alternated. When a new coating is selected the drying devices can be automatically adjusted by simply selecting drying configurations which were predetermined using graphs like those shown in FIGS. 7 and 8.

Thus since the invention disclosed herein may be embodied in other specific forms without departing from the spirit or general characteristics thereof, some of which forms have been indicated, the embodiments described herein are to be considered in all respects illustrative and not restrictive. For example, while the Applicant's invention has been described as used on an on-line system, it may also be used on an off-line station, for moving or unmoving coatings. The scope of the invention is to be indicated by the appended claims, rather than by the foregoing description, and all changes which come within the meaning and range of equivalency of the claims are intended to be embraced therein.

What is claimed is:

1. A method for monitoring the drying speed of a coating applied to webs or sheets, by monitoring gel point, comprising:

projecting a focused or collimated beam of radiation at a measurement location on the coating;

examining specular radiation created by the beam of radiation which is reflected from the coating, to create a specular radiation value;

examining diffused radiation created by the beam of radiation which is diffused from the coating, to create a diffused radiation value; and comparing the specular radiation value to the diffused radiation value to extract information about a location of the gel point relative at the measurement location.

2. The method of claim 1 wherein the step of comparing the specular radiation value to the diffused radiation value examines whether the location of the gel point is before or after the measurement location on the coating.

3. The method of claim 1 wherein:

a ratio is formed from the specular radiation value and the diffused radiation value.

4. The method of claim 1 wherein:

the coating is moving relative to the collimated beam of radiation; and the extracted information is used to control the drying speed of the coating.

5. The method of claim 1 wherein:

the coating is moving relative to the collimated beam of radiation; and the extracted information is used to alter coating characteristics.

6. The method of claim 4 wherein:

drying speed is controlled by reducing the number or types of one or more operating drying devices, or the conditions in said drying devices.

7. The method of claim 1 wherein:

the coating is stationary relative to the collimated beam of radiation; and the extracted information is used to characterize drying characteristics of the monitored coating.

8. The method of claim 7 wherein:

the drying characteristics are used to create predetermined drying programs for an on-line gel point sensor.

9. The method of claim 7 wherein:

the drying characteristics are used to optimize coating characteristics or mill efficiency.

10. An apparatus for monitoring sheet or web characteristics, including the drying speed of a coating applied to the web or sheet, comprising:

a radiation source providing a beam of radiation;

means for directing the beam of radiation against the coating at a measurement location in a focused or collimated manner;

a first radiation detector located to receive specular radiation from said radiation source, said first radiation detector creating a specular radiation value; and a second radiation detector located to receive diffused radiation from said radiation source, said second radiation detector creating a diffused radiation value;

means for comparing the diffused radiation value to the specular radiation value, to extract information about a location of gel point relative to the measurement location.

11. The apparatus of claim 10 wherein said means for directing the beam of radiation against the coating comprises a fiber optic cable.

12. The apparatus of claim 10 wherein fiber optic cables channel diffused and specular radiation to said first and second radiation detectors from the measurement location.

13. The apparatus of claim 10 further comprising:

a further sensor means for examining at least a second sheet characteristic, said further sensor means receiving radiation from the same measurement locations as said first and second radiation detector.

14. The apparatus of claim 10 wherein:

the coating is moving relative to the collimated beam of radiation; and the extracted information is used to control the drying speed of the coating.

15. The apparatus of claim 10 wherein:

the coating is moving relative to the collimated beam of radiation; and the extracted information is used to alter coating characteristics.

16. The apparatus of claim 14 wherein:

drying speed is controlled by reducing the number or types of one or more operating drying devices, or the conditions in said drying devices.

17. The apparatus of claim 10 wherein:

the coating is stationary relative to the collimated beam of radiation; and the extracted information is used to examine the drying characteristics of the monitored coating.

18. The apparatus of claim 17 wherein:

the drying characteristics are used to create predetermined drying programs for an on-line gel point sensor.

19. The method of claim 17 wherein:

the drying characteristics are used to optimize coating characteristics or mill efficiency.

* * * * *